United States Patent [19]

Treharne, III et al.

[11] Patent Number: 4,568,337
[45] Date of Patent: Feb. 4, 1986

[54] VENTILATION TUBE PERMITTING TWO-WAY GASEOUS COMMUNICATION WITH ONE-WAY LIQUID VALVE

[75] Inventors: Richard W. Treharne, III; Anthony D. Prescott, both of Memphis, Tenn.

[73] Assignee: Richards Medical Company, Memphis, Tenn.

[21] Appl. No.: 601,310

[22] Filed: Apr. 17, 1984

[51] Int. Cl.⁴ .................... A61B 19/00; A61F 11/00
[52] U.S. Cl. ........................................ 604/247; 604/9; 128/151; 137/533.11
[58] Field of Search .............. 604/247, 264, 8–10; 137/533.11; 3/1; 128/151–152

[56] References Cited

U.S. PATENT DOCUMENTS

| | | | |
|---|---|---|---|
| 2,876,767 | 3/1959 | Wasserman | 128/151 |
| 2,888,921 | 3/1956 | Nielson et al. | 128/151 |
| 3,916,873 | 11/1975 | Wasserman | 3/1 |
| 4,052,754 | 10/1977 | Homay | 3/1.9 |
| 4,071,045 | 1/1978 | Brandt | 137/533.11 |
| 4,326,512 | 4/1982 | Peerless | 128/151 |

Primary Examiner—Stephen C. Pellegrino
Attorney, Agent, or Firm—Pravel, Gambrell, Hewitt & Kimball

[57] ABSTRACT

A myringotomy tube allowing two-way gaseous communication between an external ear canal and a middle ear cavity and only one-way liquid communication from the middle ear cavity to the external ear canal includes a ball mounted within the tube to move freely into and out of contact with a valve seat for preventing liquid from flowing into the middle ear cavity. When fluid is present in the external ear canal, fluid pressure operates to move the ball into contact with the valve seat to provide a positive seal against ingress of fluid. In the absence of fluid within the external ear canal, the ball is free to move away from the seat to permit pressure equalization and liquid drainage from the middle ear to the outer ear. Longitudinal openings are provided in the portion of the tube within the external ear canal to facilitate free passage of fluid past the ball.

11 Claims, 6 Drawing Figures

VENTILATION TUBE PERMITTING TWO-WAY GASEOUS COMMUNICATION WITH ONE-WAY LIQUID VALVE

BACKGROUND OF THE INVENTION

This invention relates primarily to prosthetic devices such as ventilation or drain tubes which are surgically inserted in the ear drum and are useful for equalizing pressure between the middle and outer ears and draining otitus media from the middle ear. More particularly, the invention relates to a one-way valve for inclusion in a ventilation tube which permits liquid, e.g. otitus media, to drain from the middle ear to the outer ear while at the same time preventing liquid from passing from the outer ear to the middle ear and permitting gaseous communication between the middle and outer ears when the valve is open for equalizing pressure between them.

By way of background, the typical remedy for middle ear effusion is a myringotomy, which is a surgical procedure that involves cutting a slit in the eardrum to alleviate a build-up or reduction of pressure in the middle ear cavity. A variety of ear ventilation tubes for insertion into such a slit have been introduced over the years. The tube primarily keeps the ear drum slit open for a sufficient period of time following the surgery to allow pressure to equalize between the middle and the outer ears. Frequently the condition of buildup or reduction of pressure in the middle ear cavity which the tube is intended to alleviate requires that the tube remain in place for a significant period of time.

One problem associated with the use of such ventilation tubes is that they may permit the ingress of potentially contaminating fluids such as water from bathing or swimming, which may aggravate the condition which the tube was intended to alleviate. For this reason, patients fitted with such ventilation tubes have been instructed to take special precautions, for example, using cotton or a wax plug to block the exterior tube opening when bathing, and ordinarily have been advised not to swim.

There are prior art ventilation tubes which have been designed to prevent liquid from entering the middle ear cavity so that the wearer is not unduly restricted in his or her activities. For example, U.S. Pat. No. 4,326,512 to Peerless teaches a ventilation tube device which includes a piston or plug for temporary insertion in the tube to permit the patient to participate in normal activities, including swimming. Although providing a partial solution to the problem, a patient-inserted device has disadvantages. For example, in the process of inserting or removing the plug, the patient may dislodge the ventilation tube, risking damage to the ear and/or requiring reinsertion of the tube. In addition, the piston or plug may cause contamination problems and aggravate the infection. Although have a physician insert the plug may minimize these risks, this would be costly and inconvenient. Furthermore, such pistons or plugs do not permit passage of fluids or gases from the middle ear to the outer while inserted, substantially preventing the ventilation tube from performing its pressure equalization and drainage functions until the plug is manually removed.

It has also been proposed to use a gas permeable-liquid impermeable covering for the exterior opening of an ear ventilation tube to prevent ingress of fluids to the middle ear, but at the same time allow pressure equalization. Examples of such membranes can be found in U.S. Pat. Nos. 3,916,873 to Wasserman, 4,094,303 to Johnston, and 4,169,697 to Cantekin. Although tubes including such membranes are acceptable for equalizing gaseous pressure between the middle and outer ear, these membranes do not permit fluid drainage from the middle to outer ear. For this reason, they are not suitable for applications where the wearer's condition includes fluid build-up in the middle ear or the potential for such build-up. Not only would they not permit drainage, but should fluid build-up occur, the fluid pressure may cause expulsion of the ventilation tube requiring surgical reinsertion.

Although various types of valves have been used in devices implanted in the human body, they all relate to controlling the flow of liquids and require significant fluid pressure to control the valve. None is known which is designed to allow two-way gaseous communication when the valve is open and restrict liquid flow to one direction, and is designed to operate with minimal fluid pressure. Such liquid valves are taught in U.S. Pat. Nos. 3,926,215 to Macleod and 4,319,364 to Kaster where generally pivotally mounted two-way disc valves permit free fluid flow in one direction and restrict, without completely blocking, fluid flow in the opposite direction. U.S. Pat. No. 3,997,923 to Possis describes a two-way ball-type valve also for restricting fluid flow in one direction, and is primarily directed toward a permanent housing for the valve which permits replacement of the valve mechanism without removing its associated housing. U.S. Pat. No. 3,768,102 to Kwan-Gett, et al. teaches an artificial urethral valve including a ball and spring arrangement which requires a relatively high breakaway or opening force to open the valve, and thereafter a constant outflow of fluid to maintain the valve in its open position. These types of valves are not suitable for applications where significant fluid pressure is not available on both sides of the valve or where a valve is designed to remain open unless liquid pressure on one side forces it to close.

SUMMARY OF THE INVENTION

According to the present invention, a prosthetic device such as a ventilation tube for the middle ear has been developed which includes a valve that permits the free flow of gases in both directions through the tube. The valve also permits fluids which might build up in the middle ear to escape through the tube, but which automatically blocks the flow of any liquid from outside the ear to the middle ear.

The ventilation tube designed in accordance with the invention includes a valve member in the form of a ceramic ball which cooperates with a valve seat so that the ball moves freely within the tube in an open position between the outer end of the tube and the valve seat under normal conditions. When liquid enters the outer end of the tube as a result of the wearer bathing or swimming, the liquid moves the ball toward and into sealing engagement with the valve seat to provide a positive seal against ingress of liquid through the tube. Gaseous communication between the outer and middle ear is maintained while the valve is in its open position through slots or perforations provided through the wall of the ear tube in the outer portion of the tube, but is stopped when the valve is closed.

With this arrangement, the ball member can freely move within the tube between an outer portion which is in communication with the atmosphere and the valve seat member when the valve is open, but when liquid enters the exterior end portion, the liquid causes the ball to move toward the valve seat into its closed position effectively to prevent the ingress of potentially contaminating liquid. When no such liquid is present, the tube remains open to permit gaseous and one-way liquid communication between the middle ear and outer ear.

BRIEF DESCRIPTION OF THE DRAWINGS

A better understanding of the invention can be had when the detailed description of a preferred embodiment set forth below is considered in conjunction with the drawings, in which.

DETAILED DESCRIPTION OF A PREFERRED EMBODIMENT

Figure 1:
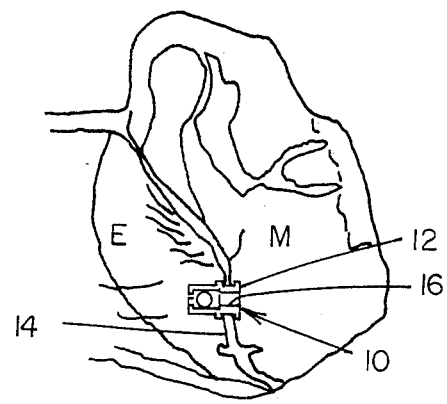
FIG. 1 is a section of the middle ear showing a preferred embodiment of a myringotomy tube of the present invention in place.

Referring to the drawings, a preferred embodiment of the ventilation tube of the present invention will be described in detail. FIG. 1 illustrates a myringotomy tube 10 which has been inserted through a surgical incision designated by reference numeral 12 through tympanic membrane or eardrum 14. The tube 10 is illustrated in its normal, open position permitting free flow of gaseous fluid in both directions between middle ear cavity M and external ear canal E through a passageway 16 within the tube 10 for equalizing pressure between the middle ear cavity M and the external ear canal E. The tube 10 is designed also to permit the flow of liquid outwardly from the middle ear cavity M to the external ear canal E for permitting drainage of otitus fluid from the middle ear cavity. However, as described in greater detail below, liquid is restricted from flowing in the other direction into the middle ear cavity so that the wearer of the tube can go swimming or take shower baths without fear of water entering the middle ear cavity M.

Figure 2:
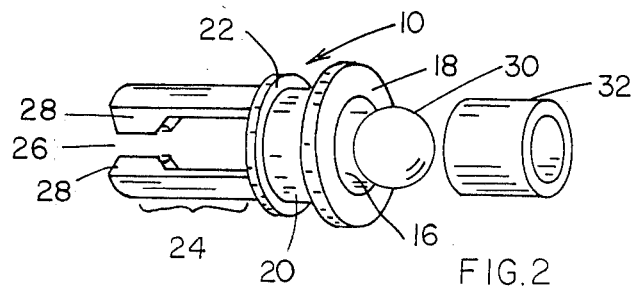
FIG. 2 is an exploded perspective view of the tube shown in FIG. 1.

With reference to FIG. 2, the tube 10 includes an inner flange 18 for preventing spontaneous extrusion of the tube 10 out of the tympanic membrane 14 (shown in FIG. 1 only), a neck portion 20 which functions to maintain the surgical incision in its open position after insertion of the tube 10, and an outer flange 22 for preventing the tube from migrating into the middle ear cavity. An exterior end portion 24 of the tube 10 is shown having several longitudinal slots 26 for allowing fluid to flow through the tube 10 when it is open. The end portion 24 is formed with stop members 28 at its outer end for maintaining a ball 30 within the end portion 24, the ball 30 operating as the valve member to open and close the tube 10 as described below.

The ball 30 is sized to move freely within the passageway 16. The stop members 28 prevent the ball 30 from moving out of the exterior end portion 24. A ring 32 is friction fitted within the passageway 16 of the tube 10 for holding the ball 30 within the tube 10 and at the same time operating as a valve seat for the ball 30. The ring 32 is fitted tightly enough so that once it is in place it cannot be removed unless force is applied to it which is much greater than can be exerted by the ball 30.

Figure 3:
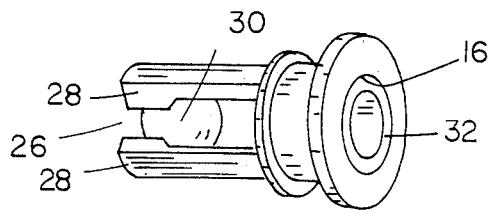
FIG. 3 is a perspective view of the assembled tube of FIGS. 1 and 2, showing the valve in its open position.
Figure 4:
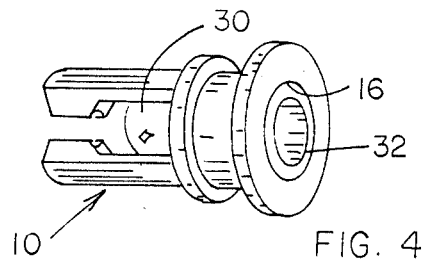
FIG. 4 is a view similar to FIG. 3 showing the valve in its closed position.
Figure 5:
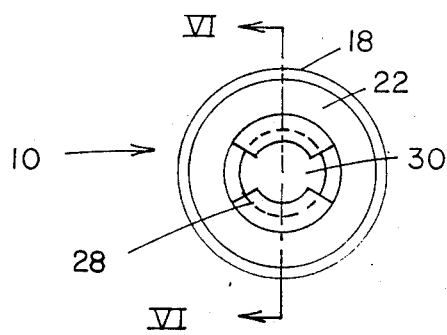
FIG. 5 is an end view of the tube shown in FIG. 4, as viewed from the right in FIG. 4.
Figure 6:
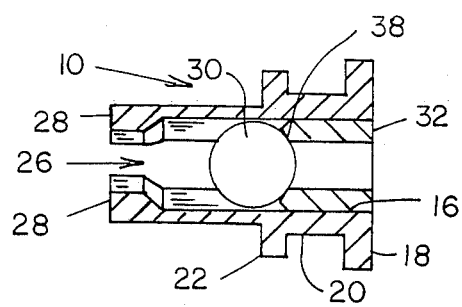
FIG. 6 is a cross-sectional view looking in the direction of the arrows along sectional line VI—VI of FIG. 5.

Referring to FIGS. 3 and 4, when there is no fluid pressure at the exterior end portion 24 of the tube 10, the ball 30 is free to move within the passageway 16 between the stop members 28 and the end face 38 of the ring 32. In this manner, fluid in the form of gas is free to move in both directions through the tube 10 to equalize pressure between the middle ear cavity M and the external ear canal E and liquid can move from the middle ear cavity outwardly through the passageway 16 to permit drainage. However, when liquid is present at the exterior end portion 24, as illustrated in FIG. 4, the liquid moves the ball 30 into contact with the inner end of the ring 32 thereby blocking the passageway 16. In this manner, liquid in the external ear canal E is prevented from entering the middle ear cavity M, as for example when the patient is bathing or swimming. The inner end of the ring 28 is preferably chamfered as designated by reference numeral 38 and shown in FIG. 6, more positively to engage the ball 30 when liquid is present in the exterior end portion 24. When the liquid is no longer present, the ball 30 is free to move away from the ring end face 38 and permit free communication between the middle ear cavity and external ear canal, as shown in FIG. 3.

The tube 10 is formed of Teflon or other suitable biocompatible material by machining or casting techniques. The ball 30 is a commercially available ceramic ($Al_2O_3$) sphere which was ground to assure its substantially spherical configuration. Other biocompatible materials can also be used, provided that the outer surface is smooth and round enough to seal the tube opening. The ring 32 is formed of 316L-type stainless steel which was machined for an interference fit within the interior end portion 34 of the tube 10, and also machined to form the chamfered end face 38. The slots 26 in the exterior end portion 24 were cut and sized to assure retention of the ball 30 within the exterior end portion 24 while maximizing flow of fluid and gases about the ball 30 in the absence of liquid in the exterior end portion 24.

For the purpose of illustrating typical dimensions for a myringotomy tube, it should be appreciated that the overall length of the tube 10 as measured along its longitudinal axis is preferably a nominal 0.142 inch (3⅛ millimeters). The passageway 16 is about 0.05 inch (1.27 millimeters) in diameter with the flange 28 having an interior diameter of about 0.02 inch (0.51 millimeters). The ring 32 has an interior diameter of about 0.04 inch (1.02 millimeters). The end face 38 is chamfered with an inside angle of about 30° and an outside angle of about 45°. The ball 30 has a diameter of about 0.047 inch (1.2 millimeters).

The foregoing description of the invention is illustrative and explanatory thereof, and various changes in the size, shape and materials, as well as in the details of the illustrated construction may be made without departing from the spirit of the invention.

We claim:

1. A prosthetic device for permitting two-way gaseous communication between the atmosphere and a body cavity of an animal body and at the same time allowing only one-way liquid flow from the body cavity to the atmosphere, comprising:

a tube having an outer end portion adapted to communicate with the atmosphere and an inner end portion adapted to communicate with a body cavity;

holding means for holding the tube in place in the animal body relative to the body cavity;

valve means mounted on said tube movable between an open position and a closed position, the valve means including means for permitting two-way gaseous flow between the atmosphere and the body cavity when the valve means is in its open position; and the valve means further including a valve opening and a closure means for closing the valve opening on the atmosphere side of the valve opening when subjected to liquid pressure from the outer end portion and allowing one-way liquid flow from the body cavity to the atmosphere in the absence of liquid pressure at the outer end portion greater than pressure on the body cavity side of the closure means.

2. The prosthetic device of claim 1, wherein said closure means includes a ball and the valve opening including an opening at the inner end of the tube which is smaller than the ball, the ball being sized to move in the tube into and out of contact with the opening for opening and closing the valve.

3. The prosthetic device of claim 2, wherein the opening is formed of a ring friction fitted within the tube.

4. The device as set forth in claim 3, wherein said ring includes a chamfered edge for engaging said ball.

5. The device as set forth in claim 4, wherein said ball is ceramic.

6. The prosthetic device of claim 2, wherein the outer end of the tube includes means for holding the ball in the tube and means for allowing gases to move through said outer end.

7. The prosthetic device of claim 6, wherein said means for allowing gases to move includes longitudinal slots formed along in said outer end portion.

8. An improved myringotomy tube having an inner end portion adapted to communicate with a middle ear, an outer end portion adapted to communicate with an external ear canal through the tympanic membrane, portion of the ear, and means for holding the tube in the tympanic membrane, the tube being of the type which includes a passageway therethrough for communicating the middle ear with the external ear canal subsequent to said tube having been inserted through a surgical incision applied to the tympanic membrane, the improvement comprising:

a ball movable in said passageway;

means for preventing the ball from moving out of the outer end portion of the tube; and means for allowing fluid to pass from the inner end portion toward the outer end portion; and a valve seat for engaging the ball to prevent liquid flow between the outer and inner end portions when the ball is in engagement with the valve seat, the ball being located on the outer ear side of the valve seat.

9. The myringotomy tube of claim 8, wherein the fluid passage means includes an opening formed in the outer end portion.

10. The myringotomy tube of claim 8, wherein the means for preventing includes stop means projecting into the passageway.

11. The myringotomy tube of claim 8, wherein the valve seat includes a ring friction fitted in the passageway.

* * * * *